United States Patent
Fava et al.

(10) Patent No.: US 8,998,837 B2
(45) Date of Patent: *Apr. 7, 2015

(54) APPARATUS FOR EXTRACORPOREAL BLOOD TREATMENT

(71) Applicant: Gambro Lundia AB, Lund (SE)

(72) Inventors: Massimo Fava, Mirandola (IT); Mauro Suffritti, Medolla (IT); Anna Puppini, Mirandola (IT)

(73) Assignee: Gambro Lundia AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/934,728

(22) Filed: Jul. 3, 2013

(65) Prior Publication Data

US 2013/0292313 A1 Nov. 7, 2013

Related U.S. Application Data

(63) Continuation of application No. 12/514,141, filed as application No. PCT/IB2006/003215 on Nov. 15, 2006, now Pat. No. 8,480,609.

(51) Int. Cl.
*A61M 37/00* (2006.01)
*A61M 1/16* (2006.01)

(52) U.S. Cl.
CPC .......... *A61M 1/1694* (2013.01); *A61M 1/1658* (2013.01); *A61M 2205/3331* (2013.01)

(58) Field of Classification Search
USPC ............ 604/4.01–6.16, 31; 422/44–45; 210/85–88, 104, 645–647
See application file for complete search history.

(56) References Cited

U.S. PATENT DOCUMENTS

| 3,626,670 A | 12/1971 | Pecker |
| 4,348,280 A | 9/1982 | George et al. |
| 4,371,385 A * | 2/1983 | Johnson .......................... 96/196 |
| 5,041,215 A | 8/1991 | Chamberlain et al. |
| 7,588,722 B2 * | 9/2009 | Chevallet ........................ 422/44 |
| 8,029,454 B2 * | 10/2011 | Kelly et al. .................. 604/5.01 |
| 8,480,609 B2 * | 7/2013 | Fava et al. .................... 604/6.09 |
| 2005/0011833 A1 * | 1/2005 | Stahl ............................ 210/646 |

FOREIGN PATENT DOCUMENTS

| EP | 0796997 | 9/1997 |
| FR | 2712822 A1 | 6/1995 |

* cited by examiner

*Primary Examiner* — Philip R Wiest

(74) *Attorney, Agent, or Firm* — K&L Gates LLP

(57) ABSTRACT

An apparatus (1) for extracorporeal blood treatment comprising a blood treatment device (2) having a semipermeable membrane (5) which separates a blood chamber (3) from a fluid chamber (4). A used fluid line (7) connects the fluid chamber to a used fluid discharge. A first pump (8) controls the ultrafiltration through the semipermeable membrane. A second pump (9) arranged in the used fluid line downstream of the first pump keeps pressure between the first and the second pump at a constant predetermined value. The invention provides a protection system against any possible pressure change in the used fluid discharge in a hemodialysis or hemo(dia)filtration apparatus.

15 Claims, 1 Drawing Sheet

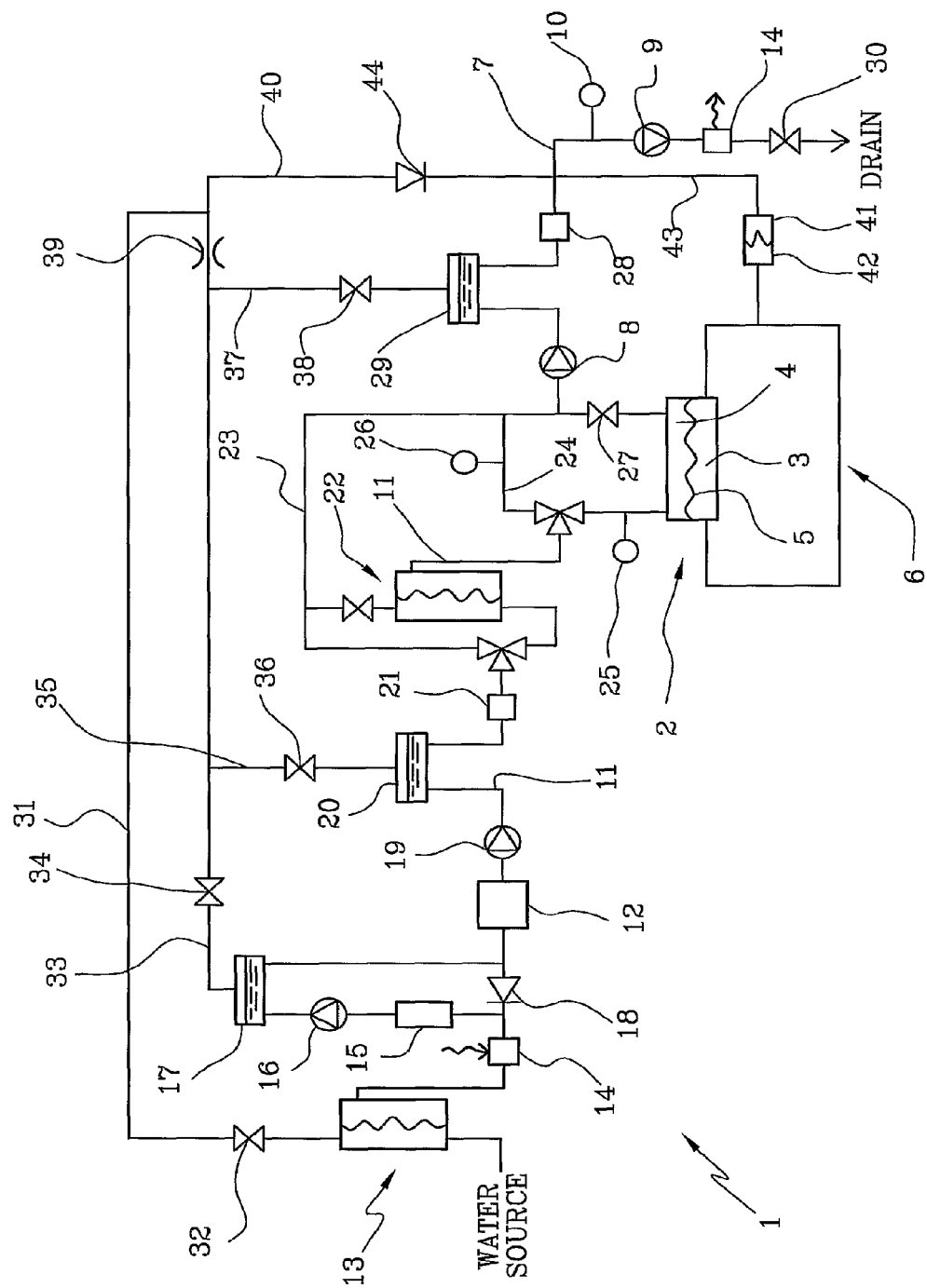

APPARATUS FOR EXTRACORPOREAL BLOOD TREATMENT

BACKGROUND OF THE INVENTION

The present invention relates to an apparatus for extracorporeal blood treatment.

Specifically, though not exclusively, the invention can be usefully applied in an apparatus for treating kidney failure (hemodialysis and/or hemo(dia)filtration).

In particular the invention relates to an extracorporeal blood treatment apparatus as defined in the preamble of claim 1.

Such an apparatus is already disclosed in U.S. Pat. No. 4,348,280, which describes a dialysis machine provided with means for continuous preparation of dialyzing liquid by mixing water with dialysis concentrate. The dialysis machine includes a device for removing and minimizing gas in the dialysis liquid, as well as means for controlling pressure and flow rate of the dialysing liquid in the dialyzer. The means for controlling comprise a first flow rate limiter which is located upstream of the dialyzer and a second flow limiter located downstream of the dialyzer. The degassing device comprises a degassing reservoir which is continuously under a negative pressure supplied by two pumps: the first pump removing gas from the tank and the second removing degassed water from the tank. The pressure in the degassing reservoir is therefore unrelated to the dialysing liquid rate. The first gas pump is a constant speed pump producing a negative pressure in the degassing reservoir which is not affected by the flow rate of liquid to be degassed. The first gas pump is arranged on the drainage line connecting the dialyzer outlet to the discharge. The first pump is therefore useful both for applying a negative pressure on the degassing reservoir and for aspirating the used dialysis liquid from the dialyzer. The above mentioned prior art machine has the drawback of being unable to permit either a precise control over the gas quantity which has been removed from the dialysis liquid, or a regulation of the percentage of gas contained in the dialysis liquid operating inside the dialyzer. A further drawback is that it cannot estimate variation in the fluid flow rate through the vent line of the degassing reservoir.

SUMMARY OF THE INVENTION

A purpose of the invention is to provide an apparatus for extracorporeal blood treatment provided with a system for fluid aspiration, which apparatus is independent of the operative conditions (particularly pressure and treatment fluid flow rate) in the blood treatment device.

A further purpose of the invention is to provide a device which is constructionally simple and economical.

An advantage of the invention is that it provides an apparatus whose operating conditions are not affected by the situation (especially by the pressure level) at the discharge of the used treatment fluid.

The invention also has the advantage of providing, in a blood treatment apparatus, a fluid aspiration system which is highly versatile, reliable, effective, easily adaptable to many possible uses, among which the evacuation of the liquid used for the tangential flushing of the ultrafilters, or the evacuation of fluids from various parts of the apparatus (such as gas evacuation from the degassing system upstream and/or downstream of the blood treatment device, or liquid and gas evacuation from the extracorporeal circuit during the priming stage).

A further advantage of the invention is that it provides a device which is equipped with a protection system for the hydraulic circuit against any possible pressure change in the used treatment fluid discharge.

These aims and more besides are all attained by the invention as it is characterized in one or more of the following claims.

Further characteristics and advantages of the present invention will better emerge from the detailed description that follows, of at least one preferred but not exclusive embodiment of the invention, which is described by way of non-limiting example in the appended figures of the drawings.

BRIEF DESCRIPTION OF THE DRAWINGS

In the following description reference is made to the appended drawings, which are provided by way of example and therefore have no limiting purpose and in which FIG. 1 schematically shows the apparatus of the invention.

DETAILED DESCRIPTION

In FIG. 1, 1 denotes in its entirety an apparatus for extracorporeal blood treatment. In this specific case the apparatus is an apparatus for treating kidney failure, more particularly a hemodialysis apparatus. The invention is usable in any kind of hemodialysis and/or hemo(dia)filtration apparatus. In this specific case, in order to provide a clear and simple explanation, not all the components of a hemodialysis or hemo(dia) filtration apparatus, will be explicitly described, such as the disinfection system, the blood loss detection system, the monitoring and control system for the various parameters of the apparatus (such as temperature, conductivity, pH, pressure etc. in the dialysis fluid), the substitute fluid infusion system in case of hemo(dia)filtration etc.

The apparatus 1 comprises a blood treatment device 2 (dialyzer or hemo(dia)filter) having a blood chamber 3, a fluid chamber 4 and a semipermeable membrane 5 which separates the blood chamber 3 from the fluid chamber 4.

The apparatus 1 comprises a prior art extracorporeal blood circuit which is known and denoted in its entirety by 6, for connecting the blood chamber 3 to a patient's vascular access (not shown) during treatment. The extracorporeal circuit 6 comprises any extracorporeal circuit usable for blood circulation in a hemodialysis and/or hemo(dia)filtration apparatus. In particular the extracorporeal blood circuit comprises an arterial blood line for removing blood to be treated from the vascular access and sending it to chamber 3, and a venous blood line to return the treated blood from blood chamber 3 to the vascular access. Each blood line (arterial or venous) comprises a device end with a connection to blood chamber 3 and a patient end with a connection to the vascular access. Each blood line (arterial and venous) also has the various elements (expansion chambers, clamps, service lines, syringe accesses, etc.) which a blood line is normally provided with; in this description these elements are not described in order to provide a short and clear exposition. FIG. 1 shows the blood extracorporeal circuit 6 in a priming configuration.

The apparatus 1 comprises a used fluid line 7 for connecting the fluid chamber 4 to a used fluid discharge. A first actuator is predisposed in the used fluid line. The first actuator is in particular a first fluid circulation pump 8, which, when operating, is able to change pressure and flow rate of the fluid crossing the fluid chamber 4. This first pump 8 is a positive displacement pump (for instance a gear pump).

A second actuator is arranged in the used fluid line 7 downstream of the first actuator. The second actuator is in this case a second fluid circulating pump 9, in particular a positive displacement pump (for instance a gear pump). The second actuator, which is arranged in series with the first actuator along line 7, is capable, in particular, of varying a pressure in an intermediate tract of the used fluid line 7, i.e. in the tract between the first and the second actuator.

The apparatus 1 comprises a first pressure sensor 10 designed to emit a pressure signal indicating pressure in the above-mentioned intermediate tract of the used fluid line 7. In the specific case the pressure sensor 10 is arranged along the used fluid line 7 upstream of the second pump 9.

The apparatus 1 comprises a control unit (not shown) programmed to control the second pump 9 in accordance with the above-described pressure signal. In particular the control unit controls the second pump 9 in feedback so as to keep pressure upstream of the second pump 9 at a desired value; the desired value can change according to need, situation or operating mode of the apparatus; besides, the desired pressure value can be constant or can be changed according to predetermined criteria.

The apparatus comprises a fresh fluid line 11 for connecting a source of a treatment fluid to the fluid chamber 4 and/or to the extracorporeal blood circuit 6 (depending on whether the treatment is hemodialysis or hemo(dia)filtration). In this particular case the fresh fluid line 11 is connected to a device for preparing a treatment fluid, which is schematically shown and globally referred to as 12. The preparation device can be any device for preparing a treatment fluid (such as a dialysis or a substitute fluid). In particular the preparation device 12 is specially designed to prepare a treatment fluid by mixing water with solid and/or liquid concentrates. The fresh fluid line 11 in this case has an initial tract connecting the preparation device 12 to a water source. The initial tract is equipped with a first ultrafilter 13 having a retentate chamber (upstream chamber) connected to a source of a fluid to be ultrafiltrated (water), a filtrate chamber (downstream chamber) connected to the fluid chamber 4 through the preparation device 12, and a semipermeable membrane, for instance of the hollow fibre bundle type which separates the retentate chamber from the filtrate chamber. The apparatus 1 comprises a pressure regulator (not shown) predisposed in the fresh fluid line 11 before the first ultrafilter 13. The pressure regulator controls the downstream pressure at a predefined pressure. The pressure regulator maintains the downstream pressure at the predefined pressure irrespective of the upstream pressure (i.e. the pressure at the water source). The pressure regulator may control the downstream pressure by restricting the flow. The pressure regulator may be manually adjusted at the predefined downstream pressure. The apparatus 1 further comprises an inlet valve (not shown) arranged in the fresh fluid line 11 between the pressure regulator and the first ultrafilter 13. The inlet valve is normally closed and is opened to allow water supply.

The apparatus 1 also comprises a heat exchanger 14 predisposed after the first ultrafilter 13 in order to recover heat from the used treatment fluid. After the heat exchanger 14 the fresh fluid line 11 has a degassing (and heating) loop of the fluid (water) including a heater 15, a degassing pump 16, and a first liquid-gas separator 17 (degassing chamber). A temperature sensor (not shown) controls the heater 15. A degassing choke (not shown) causes a lowering of the water pressure and a subsequently easier water degassing in the separator 17. On the main line (fresh fluid line 11) a check valve 18 prevents the fluid flow from a first branch point (removal of water to be degassed) of the degassing loop to a second branch point (degassed water return) of the same loop placed upstream of the first branch. The fresh fluid line 11 is further provided with a supply pump 19 (for example of the gear pump type) to circulate fluid in the same line to the fluid chamber 4. A second liquid-gas separator 20 (degassing chamber) is arranged on line 11 downstream of the preparation device 12 to degas the treatment fluid. A first flow sensor 21 is placed downstream the second separator 20 to emit a signal indicating the flow rate in the fresh fluid line 11. A second ultrafilter 22 is arranged before the fluid chamber 4 in order to ultrafilter the treatment fluid. A first by-pass line 23 is arranged upstream of the second ultrafilter 22, while a second by-pass line 24 is arranged downstream of the second ultrafilter 22. Each by-pass line 23 and 24 by-passes the fluid chamber 4 and puts the fresh fluid line 11 in communication with the used fluid line 7. Each by-pass line 23, 24 is provided with a by-pass valve (in this particular case a three-way valve in order to selectively open or shut the by-pass line and the main line). A pressure sensor upstream 25 and a pressure sensor downstream 26 are pre-arranged to measure pressure respectively on the inlet and outlet of the fluid chamber 4. An on-off valve 27 can shut the outlet of the fluid chamber 4 on command of the control unit.

A second flow sensor 28 is predisposed to send to the control unit a signal indicating the fluid flow rate in the used fluid line 7. The control unit operates the first pump 8 according to the flow rate signal emitted by the second sensor 28 in order to achieve a desired fluid balance in the treatment device 2. The fluid balance depends, as is known, on the fluid flow rate through the membrane 5 (ultrafiltration rate), which rate results from the difference between the flow rates measured by the flow sensors 28 and 21. In order to get the desired fluid balance, the rate signal emitted by the first sensor 21 can be used, as known, to command the supply pump 19 or the first pump 8. A third liquid-gas separator 29 (degassing chamber) is arranged on the used fluid line 7 upstream of the second flow sensor 28. The used fluid line 7 is also provided with an on-off valve 30 located downstream of the second pump 9.

The apparatus 1 comprises a fluid balance control device or fluid balance system for controlling the ultrafiltration rate through the membrane 5. The fluid balance system includes in this case the first flowmeter 21, the second flowmeter 28, and the first pump 8. In other embodiments (not shown) the fluid balance system may be of different (known) type, e.g. a system comprising an equalizing device (with equalizing volumetric chambers, or with equalizing flowmeters, or of another type) and an ultrafiltration line bypassing the equalizing device.

The intermediate tract of line 7 between the first pump 8 and the second pump 9 is kept at a desired pressure by controlling the second pump 9 in accordance with the signal emitted by the pressure sensor 10. The intermediate tract is connected or designed to be connected to various elements of the apparatus 1. Firstly the above mentioned intermediate tract is connected to an outlet of the retentate chamber of the first ultrafilter 13 through a tangential flushing line 31. The flushing line 31 is used for the tangential washing of the first ultrafilter 13. A flushing valve 32, arranged on the flushing line 31, is periodically opened in order to carry out the tangential washing. Secondly, the intermediate tract is connected to a gas outlet (vent) of the first separator 17 through a first vent line 33 provided with a first vent valve 34. The intermediate tract is further connected to a gas outlet (vent) of the second separator 20 through a second vent line 35, provided with a second vent valve 36. The above-mentioned intermediate tract is also connected to a gas outlet (vent) of the third separator 29 through a third vent line 37 provided with a third vent valve 38. The various vent lines 33, 35, 37 are connected to the intermediate tract through a single restrictor choke 39, which serves all lines. The choke 39 is formed by a fixed pre-calibrated section restriction. The various vent lines 33, 35, 37 unite to the flushing line 31 to form a unique main branch line 40 which branches from a branch point of the used fluid line 7, the branch point of used fluid line 7 being located between the second flow sensor 28 and the second pump 9. Each vent valve 34, 36, 38 is opened and shut according to a predetermined rule (for instance periodically, or depending on the liquid level or on the pressure level in the corresponding separator 17, 20, 29). The branch line 40 is provided with a check valve 44 to prevent return flow to the separators and to the ultrafilter.

The intermediate tract between pump 8 and pump 9 is further connected to a connection port 41 suitable for connection to an access port 42 to the extracorporeal circuit 6. The connection between port 41 and port 42 is a seal connection. The connection between port 41 and port 42 is removable. The connection between port 41 and port 42 includes the connection disclosed in U.S. Pat. No. 5,041,215 (which is herein incorporated by reference) between drain 32 and, respectively, priming cap 44 (reference numbers as cited by U.S. Pat. No. 5,041,215). (The connection between port 41 and port 42 may include, in other embodiments not shown, a screw connection, particularly of the luer type, or other known removable connections). The connection port 41 is arranged on the external panel of the hemodialysis or hemo(dia)filtration apparatus. The access port 42 comprises, in this particular case, a connection placed on a patient end of one of the blood lines of the extracorporeal circuit 6, for instance the arterial line or the venous line. Alternatively the access port 42 can be a connection arranged in a branch-off relationship with the arterial or venous blood line. The access port 42 can be, for example, a connection arranged on a service line connected to the arterial line or to the venous line; in particular the service line can be connected to an arterial or venous blood expansion chamber. The configuration in which ports 41 and 42 are connected to each other (as in FIG. 1) is used particularly in the priming stage of the extracorporeal circuit in order to perform fluid evacuation (air and a part of the priming liquid used) through the discharge of the treatment apparatus 1. In this case the second pump 9 is used for the aspiration of both the air and the used priming liquid. The connection port 41 is connected to a discharge line 43 branching out from a branch point of the used fluid line 7, the branching point being located between the second flow sensor 28 and the second pump 9. The priming liquid can be sourced by connecting the extracorporeal circuit to a priming liquid container (for example a saline solution bag), or by backfiltrating a sterile liquid (for example dialysis fluid) from the fluid chamber 4 to the blood chamber 3. In case of backfiltration a difference in pressure between the fluid chamber 4 and the blood chamber 3 is generated for instance by aspiration via the second pump 9 and/or by aspiration using a blood pump associated to the extracorporeal circuit 6.

The second fluid circulation pump 9 is arranged along the main pathway of the used treatment fluid. The second pump 9 is arranged in series with the first pump 8. The inlet of the second pump 9 is designed to receive the used fluid (the entire amount or essentially the entire amount of the used fluid, eventually minus the weight loss) coming from the outlet of the first pump 8. The second pump 9 does not control the ultrafiltration through the membrane 5. The second pump 9 is not responsible for the fluid balance. The second pump 9 is not part of the fluid balance system of the apparatus. The second pump 9 is placed downstream the first pump 8. The second pump 9 is placed between the used fluid discharge and the first pump 8. The second pump 9 is used to protect the hydraulic circuit of apparatus 1 from any possible pressure change in the used fluid discharge. In particular the second pump 9 has a protective role of the fluid balance system, the circuit gas evacuation system, the flushing system of an ultrafilter, and the used priming liquid evacuation system. In short the second pump 9 acts to uncouple the discharge of the used fluid line 7 (whose conditions are sometimes uncontrollable, unpredictable, considerably changeable from one clinic to another) from the various operative elements of the apparatus 1, so that any pressure change at the discharge does not perturb the rest of the apparatus 1. For example, the second pump 9 can keep the pressure measured by the sensor 10 at a constant level (for instance about 0 mmHg during treatment), or can act so that pressure change occurs according to a predetermined sequence (in particular with negative values, i.e. values lower than 0 mmHg, in the priming stage of the extracorporeal circuit 6). The second pump 9 operates in order to keep a constant pressure, particularly at a predetermined value (for instance about 0 mmHg), at the branch point of the fluid line/s communicating with one or more operative elements of the apparatus, where the operative elements can comprise a gas-liquid separator of the treatment fluid circuit, a blood line or a service line of the extracorporeal circuit, an ultrafilter of the treatment fluid circuit, etc.

In a further embodiment of the invention (not shown), the heat exchanger 14 is also arranged upstream of the second pump 9, so that it is uncoupled from and therefore not perturbed by what happens in the discharge.

The second pump 9 facilitates the venting of the separators 17, 20, 29. This keeps pressure at a relatively low level in the entire hydraulic circuit of the apparatus. In particular this keeps pressure at a relatively low level at the inlet of the fresh fluid line 11 (which is located upstream of the first ultrafilter 13, after the inlet connection connected to the municipal water supply providing water at a relatively high pressure). The inlet pressure is set by a pressure regulator (as a rule a known pressure reducer, not shown in FIG. 1) at a constant pre-set value which is high enough to enable the above mentioned separators to breathe. The aspirating action of the second pump 9 makes it possible to pre-set a relatively low value in the pressure regulator.

In a further embodiment of the invention (not shown), the supply pump 19 is arranged in the fresh fluid line 11 downstream the second gas-liquid separator 20. The supply pump 19 is arranged between the separator 20 and the first by-pass line 23, or between the separator 20 and the first flow sensor 21, or between the separator 20 and the fluid balance system, or between the first flow sensor 21 (or the fluid balance system) and the first by-pass line 23, or between the fluid balance system and the first by-pass line 23.

LEGEND 1 extracorporeal blood treatment apparatus
2 blood treatment device
3 blood chamber
4 fluid chamber
5 semipermeable membrane
6 extracorporeal blood circuit
7 used fluid line
8 first fluid circulation pump
9 second fluid circulation pump
10 first pressure sensor
11 fresh fluid line
12 treatment fluid preparation device
13 first ultrafilter
14 heat exchanger 15 heater
16 degassing pump
17 first gas-liquid separator
18 check valve
19 supply pump
20 second gas-liquid separator
21 first flow sensor
22 second ultrafilter
23 first by-pass line
24 second by-pass line
25 upstream pressure sensor
26 downstream pressure sensor
27 on-off valve
28 second flow sensor
29 third gas-liquid separator
30 on-off valve
31 tangential flushing line
32 flushing valve
33 first vent line
34 first vent valve
35 second vent line
36 second vent valve
37 third vent line
38 third vent valve
39 restrictor choke
40 branch line
41 connection port
42 access port
43 discharge line
44 check valve

The invention claimed is:

1. An apparatus for extracorporeal blood treatment comprising:
 a blood treatment device having a blood chamber, a fluid chamber, and a semipermeable membrane separating the blood chamber from the fluid chamber;
 a used fluid line configured to connect the blood treatment device to a used fluid discharge;
 a first actuator predisposed in the used fluid line, the first actuator being configured to control a pressure and/or a fluid flow rate in the fluid chamber;
 a protection system configured to uncouple pressure conditions in the blood treatment device from pressure conditions at the used fluid discharge, said protection system comprising:
  a second actuator arranged in the used fluid line between the first actuator and the used fluid discharge, the second actuator being configured to control a pressure in an intermediate tract of the used fluid line, said intermediate tract being comprised between the first actuator and the second actuator;
  a first pressure sensor configured to emit a pressure signal indicating a pressure in said intermediate tract of the used fluid line;
  a control unit programmed for controlling the second actuator to keep pressure in said intermediate tract of the used fluid line at a desired value.

2. The apparatus of claim 1, wherein the apparatus comprises further operative elements; wherein the used fluid line is configured to connect, at a branch point in the intermediate tract, at least one of said further operative elements to the used fluid discharge; wherein the protection system is configured to uncouple pressure conditions in the further operative elements from pressure conditions at the used fluid discharge.

3. The apparatus of claim 2, wherein the further operative elements comprise an extracorporeal blood circuit configured to connect the blood chamber to a vascular access of a patient.

4. The apparatus of claim 2, wherein the further operative elements comprise at least a gas liquid separator of a treatment fluid circuit.

5. The apparatus of claim 4, wherein the used fluid line is configured to connect a vent of the gas-liquid separator to the used fluid discharge.

6. The apparatus of claim 2, wherein the further operative elements comprise at least an ultrafilter of a treatment fluid circuit.

7. The apparatus of claim 3, wherein the further operative elements comprise a service line of the extracorporeal blood circuit.

8. The apparatus of claim 1, wherein the desired value of pressure in said intermediate tract is kept constant.

9. The apparatus of claim 1, wherein the desired value of pressure in said intermediate tract is about 0 mmHg during treatment.

10. The apparatus of claim 1, wherein the desired value of pressure in said intermediate tract changes according to a predetermined sequence.

11. The apparatus of claim 1, wherein the desired value of pressure in said intermediate tract is kept lower than 0 mmHg during priming.

12. The apparatus of claim 2, wherein the desired value of pressure in said intermediate tract is kept constant.

13. The apparatus of claim 2, wherein the desired value of pressure in said intermediate tract is about 0 mmHg during treatment.

14. The apparatus of claim 2, wherein the desired value of pressure in said intermediate tract changes according to a predetermined sequence.

15. The apparatus of claim 2, wherein the desired value of pressure in said intermediate tract is kept lower than 0 mmHg during priming.

* * * * *